(12) United States Patent
Kessel et al.

(10) Patent No.: US 11,538,113 B1
(45) Date of Patent: Dec. 27, 2022

(54) METHODS AND SYSTEMS FOR CLASSIFYING GENETIC PANELS

(71) Applicant: Cigna Intellectual Property, Inc., Wilmington, DE (US)

(72) Inventors: Julie B. Kessel, St. Petersburg, FL (US); Amanda Mills, Ooltewah, TN (US); Tommie D. Betbeze, Chattanooga, TN (US); Kathleen Luttrell, Wilbraham, MA (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 509 days.

(21) Appl. No.: 16/730,182

(22) Filed: Dec. 30, 2019

(51) Int. Cl.
| | |
|---|---|
| G06Q 40/08 | (2012.01) |
| G16H 15/00 | (2018.01) |
| G06F 16/11 | (2019.01) |
| G06Q 10/10 | (2012.01) |
| G16H 20/10 | (2018.01) |
| G16H 80/00 | (2018.01) |

(52) U.S. Cl.
CPC ............ *G06Q 40/08* (2013.01); *G06F 16/11* (2019.01); *G06Q 10/10* (2013.01); *G16H 15/00* (2018.01); *G16H 20/10* (2018.01); *G16H 80/00* (2018.01)

(58) Field of Classification Search
CPC ........ G16H 15/00; G16H 20/10; G16H 80/00; G06Q 40/08; G06Q 10/10; G06F 16/11
USPC ........................................................ 705/2–3
See application file for complete search history.

(56) References Cited

U.S. PATENT DOCUMENTS

| | | |
|---|---|---|
| 7,698,154 B2 | 4/2010 | Marchosky |
| 2003/0074564 A1 | 4/2003 | Peterson |
| 2004/0128165 A1 | 7/2004 | Block |
| 2005/0038675 A1 | 2/2005 | Siekman |
| 2005/0187797 A1 | 8/2005 | Johnson |
| 2005/0246200 A1 | 11/2005 | Thomson |
| 2010/0010835 A1* | 1/2010 | Johnson ................. G16H 50/20 705/2 |
| 2011/0125531 A1 | 5/2011 | Seare |

(Continued)

OTHER PUBLICATIONS

Lefebre et al., Genetics and Insurance: Challenges and Opportunities II, Apr. 15, 2019, RGA,, https://www.rgare.com/knowledge-center/media/research/genetics-and-insurance-challenges-and-opportunities-ii. pp. 1-19 (Year: 2019).*

(Continued)

*Primary Examiner* — Joy Chng
(74) *Attorney, Agent, or Firm* — Husch Blackwell LLP

(57) ABSTRACT

Methods and systems for classifying and editing insurance claims records are described. In one embodiment, a method, which can be performed by a processor, includes receiving an insurance claim record having a plurality of medical service codes, retrieving a first of a plurality of edit tables from a database, determining whether one of the plurality of medical service codes in the record matches one of a plurality of core identifier values stored in the first of the plurality of edit tables, retrieving a second of the plurality of edit tables from the database, determining whether a number of the plurality of medical service codes in the record match a plurality of confirmation values stored in the second of the plurality of edit tables, and editing the insurance claim record by including a genetic panel test medical service code in the insurance claim record.

21 Claims, 9 Drawing Sheets

(56) References Cited

U.S. PATENT DOCUMENTS

| | | | |
|---|---|---|---|
| 2013/0226621 A1* | 8/2013 | Van Der Zaag | G16H 40/20 |
| | | | 702/19 |
| 2014/0142986 A1* | 5/2014 | Oesterheld | G06Q 30/04 |
| | | | 705/2 |
| 2015/0052058 A1 | 2/2015 | Mccown | |
| 2016/0321404 A1 | 11/2016 | Ginsburg | |
| 2017/0083673 A1 | 3/2017 | Dawson, III | |
| 2019/0244688 A1* | 8/2019 | Wilson | G16H 10/40 |
| 2020/0075138 A1* | 3/2020 | Todd | G16H 15/00 |

OTHER PUBLICATIONS

Anderson et al., More Than A CPT Code: A View On Genetic Testing From Inside A Health Plan, AACC.org, https://www.aacc.org/cln/articles/2019/more-than-a-cpt-code-a-view-on-genetic-testing-from-inside-a-health-plan, Apr. 1, 2019 (Year: 2019).*

Mack, Genetic Tests: A Coverage Challenge, Jun. 15, 2015, Retina Specialist, http://www.retina-specialist.com/article/genetic-tests-a-coverage-challenge, pp. 1-6 (Year: 2015).*

\* cited by examiner

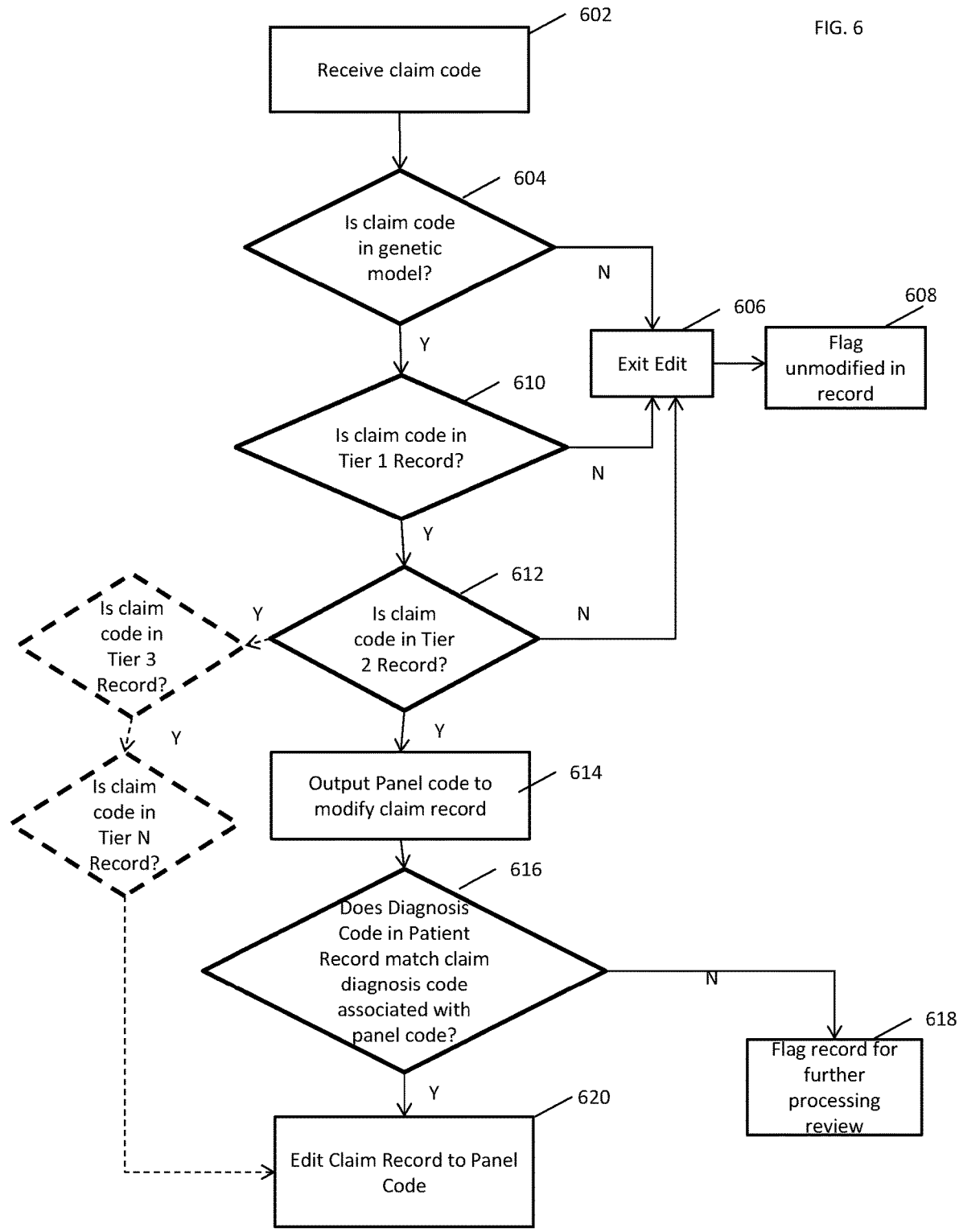

METHODS AND SYSTEMS FOR CLASSIFYING GENETIC PANELS

FIELD

The present disclosure relates generally to the technical field of data processing. In a specific example, the present disclosure may relate to classifying genetic testing panels.

BACKGROUND

The American Medical Association defined numerous current procedural terminology (CPT) codes that denote various medical services and procedures, and insurance claims can include numerous CPT codes. However, the CPT codes included in an insurance claim record may not accurately reflect the medical service provided by a medical professional, such as a doctor, a hospital, or a laboratory. Conventional insurance claim adjudication requires significant data processing to ensure that the medical service recorded in the insurance claim record accurately reflects the medical service. As such, there is a need in the field to review, fulfill or edit insurance claim records using less processing by computer systems.

BRIEF DESCRIPTION OF THE DRAWINGS

FIG. 6 is a block diagram of a flowchart illustrating methods for editing genetic testing insurance claim records, according to an example embodiment.

DETAILED DESCRIPTION

Figure 1:
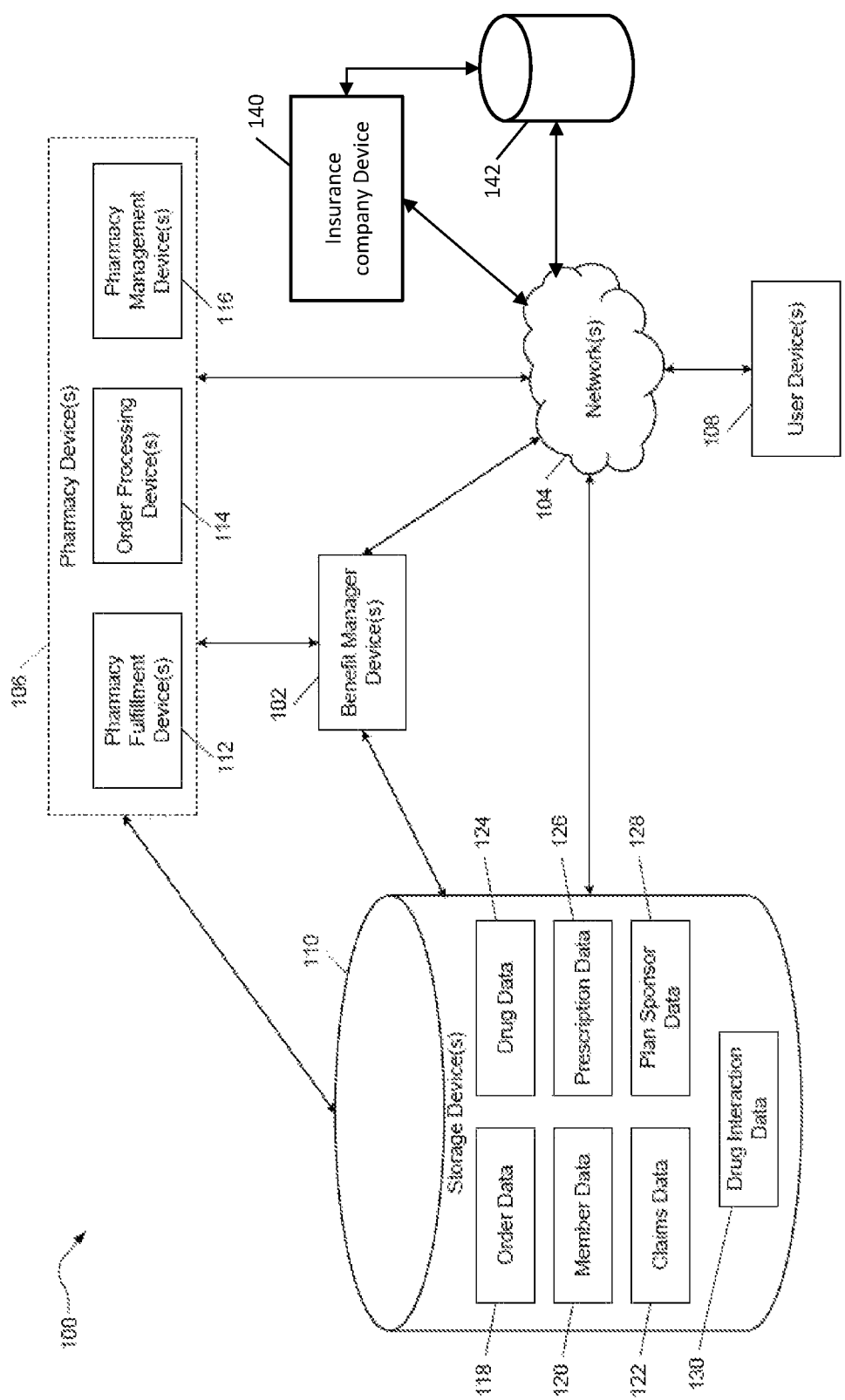
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a rare genetic disease benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The user device 108 may be a stand-alone device, or may be a multi-use device. Examples of the user device 108 include a set-top box (STB), a receiver card, a mobile telephone, a personal digital assistant (PDA), a display device, a portable gaming unit, and a computing system; however, other devices may also be used. For example, the user device 108 may include a mobile electronic device, such an IPHONE or IPAD device by Apple, Inc., mobile electronic devices powered by ANDROID by Google, Inc., and a BLACKBERRY device by Research In Motion Limited. The user device 108 also include other computing devices, such as desktop computing devices, notebook computing devices, netbook computing devices, gaming devices, and the like. Other types of electronic devices may also be used. Additionally or alternatively, the user device 108 can execute an application that may use a cellular phone function of the user device 108. The application may include instructions that when executed on the user device 108, in the benefit manager device 102, or pharmacy device 106, cause a machine to change its state or perform tasks within the machine and with other machines.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. In addition, the member data 112 can include or reference prescription numbers associated with the member.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), typical dosing instructions, etc. The drug data 124 may include information associated with a single medication or multiple medications. However, dosing instructions may come from the claims data 122 if the doctor prescribed dosing instructions different from the typical dosing instructions.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

Furthermore, the drug interaction data 130 can include all known interactions between various prescription drugs. The known interactions can be negative, positive, or benign. Further still, the drug interaction data 130 can include known interactions between each prescription drug and over-the-counter drugs, known interactions between each prescription drug and vitamins or medical herbs (e.g. St. John's Wort), or known interactions between each prescription drug and commonly used substances, such as alcohol.

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

In addition, the benefit manager device 102 may communicate with one or more insurance company device(s) 140 over the network 104. Additionally, the insurance company device 140 can communicate with the pharmacy device 106 and with the user device(s) 108 over the network 104. Each of the one or more insurance company devices 140 can be associated with a respective insurance company, which may be the same or a different entity than the PBM entity operating the benefit manager device 102. For example, the insurance company may offer insurance coverage to insured members, insured clients, or insured patients affiliated with the insurance company. As used herein, "insured members", "insured patients", and "insured clients" are members, patients, or clients of the insurance company. In some implementations, the insurance company may provide one or more benefits including a medical or health benefit, a rare genetic disease benefit, a dental benefit, a vision benefit, a wellness benefit, a radiology benefit, a pet care benefit, an insurance benefit, a long term care benefit, a nursing home benefit, etc. In addition, the insurance company may offer the pharmacy or drug benefit offered by the PBM to the insured members, insured clients, or insured patients as part of an insurance policy.

The insurance company device 140 may reference data from an associated insurance storage device 142 in making insurance decisions, such as repayment of insurance claims. The insurance storage device 142 may include: non-transitory storage (for example, memory, hard disk, CD-ROM, etc.) in communication with the insurance company device 140 directly and/or over the network 104. The insurance storage device 142 may store data similar to the storage device 110 for insurance purposes. For example, the insurance storage device 142 can store insured member data, insured claims data, insured drug data, and insured prescription data, etc. The insured data stored by the insurance storage device 142 may be similar to the data stored in the storage device 110, but the insured data may reflect business differences between the insurance company and the PBM. For example, the insured claims data may reflect prescription drug payment claims and further include claims for the payment of medical services or other medical procedures, such as surgeries, diagnostic scans, or medical testing. In some embodiments, the insured claims data or the insured member data can include ICD10 codes and CPT codes.

In addition, the insurance storage device 142 can include a plurality of edit tables. The plurality of edit tables can store a plurality of medical service codes (e.g. CPT codes) related to genetic testing. The insurance company device 140 can execute logic and compare a plurality of medical service codes in an insurance claim, which can be stored in an insurance claim record, to the medical service codes stored in the plurality of edit tables to determine whether insurance claim relate to a genetic panel test. If the insurance company device 140 determines that the plurality of medical service codes in the insurance claim record relate to one or more genetic panel tests, the insurance company device 140 can edit the insurance claim record to properly reflect the genetic panel test. After editing the insurance claim record, the insurance company can adjudicate and reimburse a medical service provider, such as a laboratory, for the genetic panel test that was performed and any other medical services included in the insurance claim record.

In some embodiments, the user device 108 can comprises a laboratory computer or other device associated with the medical laboratory performing the genetic testing. Through the network 104, the laboratory device 108 can submit the insurance claim record to the insurance company device 140 requesting reimbursement for the genetic testing performed at the laboratory on behalf of insured patients associated with the insurance company. In some embodiments, the insurance reimbursement requests can come directly from the insured patient or from a doctor of the insured patient. As such, the user device 108 can also comprise a doctor's computer terminal or a device associated with the insured patient, such as a smartphone or a personal computer.

Figure 2:
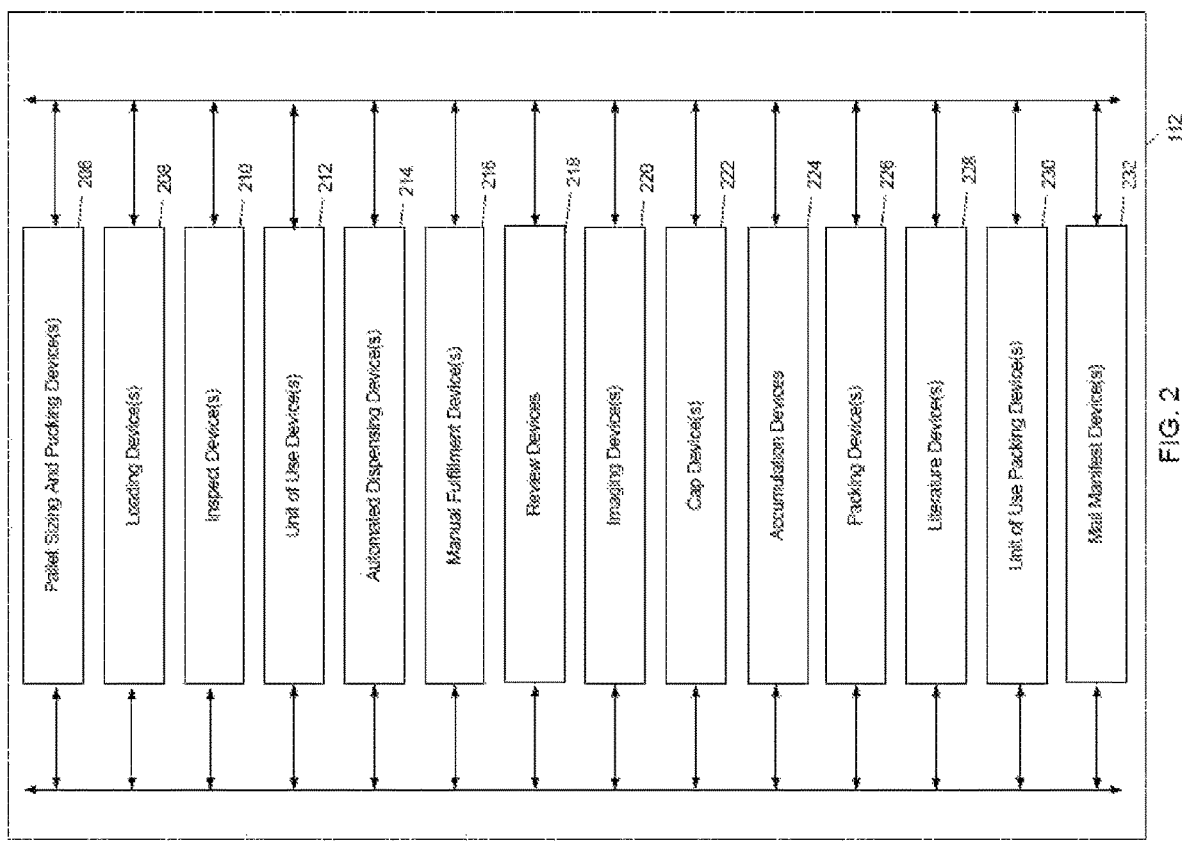
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
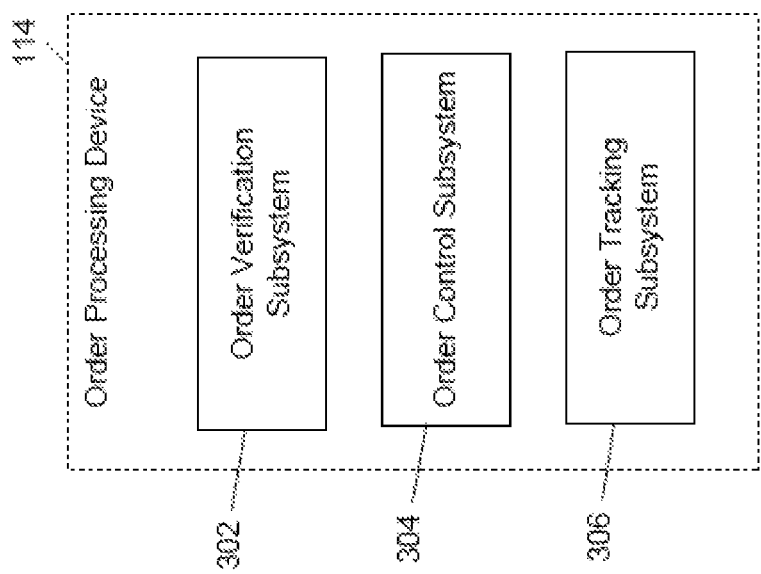
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Example methods and systems for classifying and editing insurance claim records are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Traditionally, insured patients seek genetic testing for a variety of reasons, such as confirming a diagnosis of a genetic disorder, determining a risk for cancer, or as part of family planning. For example, a common reason for genetic testing can occur when an expecting family desires to determine whether a fetus is at risk for any genetic diseases or disorders. Alternatively, the genetic testing can occur before a pregnancy to determine the risk of a genetic disorder due to a genetic pairing of a man and a woman. Regardless of the reason for genetic testing, genetic testing has become a more common procedure and one frequently covered by insurance policies due to a lowered cost created by genetic panel testing, which can test for far more genes and gene variations than conventional gene testing (e.g. exon-by-exon Sanger sequencing, also known as gene-by-gene testing).

While insurance companies may cover genetic testing, the insurance companies wish to ensure that laboratories are not overly compensated. For example, if the laboratory performs a genetic panel test testing for 300 genes or genetic conditions, the insurance company should not reimburse the laboratory for 300 individual gene-by-gene tests. Indeed, the cost to perform 300 individual gene-by-gene tests would be far more expensive than a genetic panel test. Indeed, a genetic panel test can typically cost less than even 4 or 5 gene-by-gene tests.

Because of advancing technology and economies of scale, panels are increasingly common, extensive and cost effective. Whereas in the past each test would need to be completed individually, common "platforms" allow multiple genes or gene variants or related markers to be performed concurrently. Doctors can order genetic tests from a laboratory testing for, for example, ten genes or gene variations. However, the laboratory can test for all ten genes (plus numerous other genes or gene variations) by performing a single genetic panel test. Nevertheless, even though the laboratory performed a genetic panel test, the laboratory might submit an insurance claim record that includes a plurality (e.g. ten) of medical service codes e.g. CPT, ICD10, or HCPCS or any other medical service or procedure codes) related to conventional gene-by-gene testing for the ten genes ordered by the doctor. If the insurance company fulfilled the insurance claim, which can be part of an insurance claim record, listing the plurality of gene-by-gene medical service codes, then the laboratory would receive more compensation than the actual cost to perform the genetic panel test. In this described example, the insurance claim is improper, whether due to fraud or mistake, the laboratory would be unjustly enriched, and the insurance company would needless pay additional costs to cover its policy holders.

The exemplary embodiments described herein can decipher whether an insurance claim relating to genetic testing intended to request reimbursement for a genetic panel test or actually performed a genetic panel test. Alternatively or additionally, the exemplary embodiments can determine whether a laboratory should have performed a genetic panel test so that an insurance company can reimburse the laboratory only for the genetic panel test. In response to determining an error in an insurance claim, the exemplary embodiments can edit the insurance claim record and change the procedure codes (or other medical procedure codes) in the insurance claim record to the proper genetic panel test procedure code. After editing the insurance claim record, the insurance company can properly reimburse the insurance claim for the genetic panel test.

To decipher and edit insurance claim records, the computer systems (for example, computer systems run by the insurance company) can create a plurality of edit tables listing medical service or billing codes (CPT or other medical procedure codes) for individual genetic tests. The computer system can create the plurality of edit tables through clinical investigation to relate a plurality of unbundled medical service codes, corresponding to individual gene-by-gene testing, with a single genetic panel test, and the computer system can create these tables for each genetic panel test. In some embodiments, the plurality of tables can have a hierarchy. For example, a first of the plurality of tables can have the highest rank in the hierarchy. According to an exemplary embodiment, the first of the plurality of tables can include a plurality of medical codes known as "core identifiers" because each core identifier can be uniquely associated with a single genetic panel test. The first of the plurality of tables can include a relatively small number of medical service codes (e.g. as few as two or as many as 10), and each of the medical service codes in the first of the plurality of tables can be a medical service code unique to a particular genetic panel test. In other words, each of the medical service codes in the first of the plurality of tables uniquely relates to a single genetic panel test.

The second tier in the hierarchy can include multiple tables, and the number of tables in the second tier can match or substantially exceed the number of entries or rows in the first of the plurality of tables. Each table in the second tier can include medical service codes that are associated with genes that would typically be included in a specified genetic panel test. In some embodiments, the second tier tables can comprise "confirmation codes" to confirm that the medical service codes in an insurance claim record reflect or represent a genetic panel test. Additional tiers of the hierarchy can be included to capture all medical service codes included in an insurance claim record that were or likely were part of the specified genetic panel test. In this way, the third tier of the plurality of tables can include "accessory codes" that comprise medical service codes related to tested genes or gene variations that would be reasonable to include in a genetic panel test because testing these genes is easy or inexpensively performed with a determined genetic panel test.

The tiered nature of the tables can minimize computer processing. The first tier table can include a relatively small number of entries or rows (e.g. two-10), the second tier tables can generally include more entries or rows than the first tier table, and the third tier tables can generally include more entries or rows than the second tier tables. However, the insurance company device 140 compares data in lower tier tables after omitting found codes from the insurance claim record during comparison with higher tiers. So, the computer does not needlessly process numerous codes and entries unless the lower processing steps are first performed and appropriate tests identified. Therefore, the organization of the tables into tiers decreases computer processing and more quickly results in an edit to an insurance claim record.

The plurality of tables can also include a diagnosis table storing diagnosis codes, such as ICD10 codes (or other medical diagnosis codes). The diagnosis table can relate each genetic panel test with one or more diagnosis codes associated with the genetic panel test. Then, the insurance company device can compare the ICD10 code included in the insurance claim record with the one or more diagnosis codes associated with the genetic panel test. In this way, the diagnosis table can help the insurance company device 140 determine whether the genetic panel test was medically appropriate.

Figure 4:
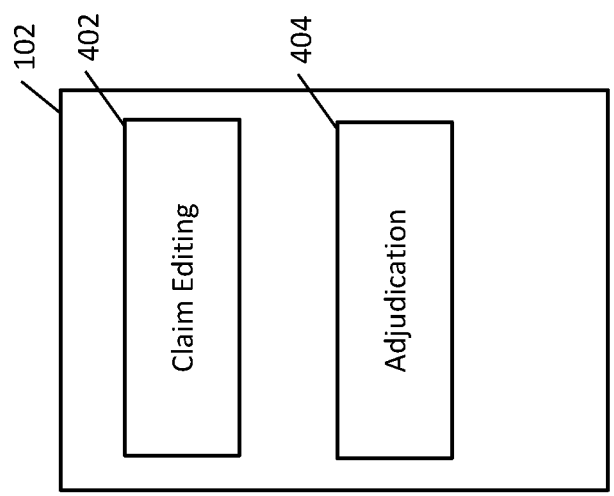
FIG. 4 is a block diagram of an example insurance company device that may be deployed within the system of FIG. 1, according to an example embodiment.

FIG. 4 illustrates the insurance company device 140, according to an example embodiment. The insurance company device 140 may be deployed in the system 100, or may otherwise be used.

The insurance company device 140 may include a claim editing subsystem 402 and an adjudication subsystem 404. The claim editing subsystem 402 can receive an insurance claim record, find and gather all the medical service codes (e.g. CPT codes) included in the insurance claim record, and reference the plurality of edit tables stored in the insurance company storage device 142 in an organized fashion to determine whether the medical service codes included in the insurance claim record suggest or relate to a genetic panel test. The claim editing subsystem 402 can reference a first of the plurality of edit tables having a first tier value and determine whether any of the medical service codes included in the insurance claim record is listed in the first of the plurality of edit tables. The claim editing subsystem 402 can also reference other edit tables based on a determination that one of the medical service codes included in the insurance claim record is listed in the first of the plurality of edit tables.

In some embodiments, the claim editing subsystem 402 can determine that one or more of the medical service codes included in the insurance claim record relate to a genetic panel test, and the claim editing subsystem 402 can edit the insurance claim record such that the one or more of the medical service codes included in the insurance claim record that relate to the genetic panel test are deleted from the claim and replaced with a medical service code related to the genetic panel test. Meanwhile, the claim editing subsystem 402 can maintain medical service codes that are unrelated to the genetic panel test in the insurance claim record.

After the claim editing subsystem 402 edits the insurance claim record, the adjudication subsystem 404 can receive the edited insurance claim record, adjudicate the insurance claim record according to insurance company rules and logic, and provide repayment to any medical service providers after performing adjudication.

Figure 5A:
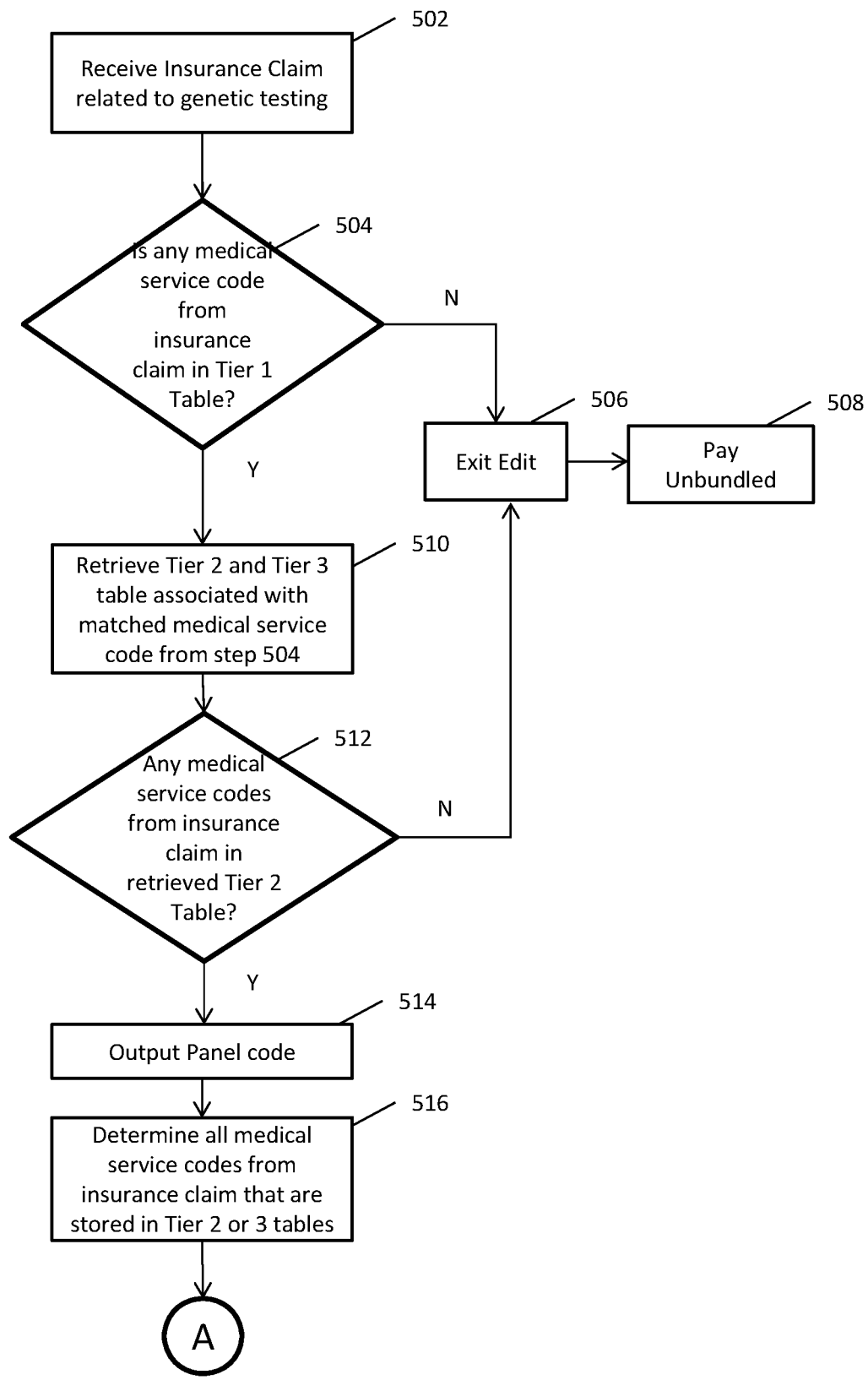
FIGS. 5A and 5B are block diagrams of a flowchart illustrating methods for editing genetic testing insurance claim records, according to an example embodiment.
Figure 5B:
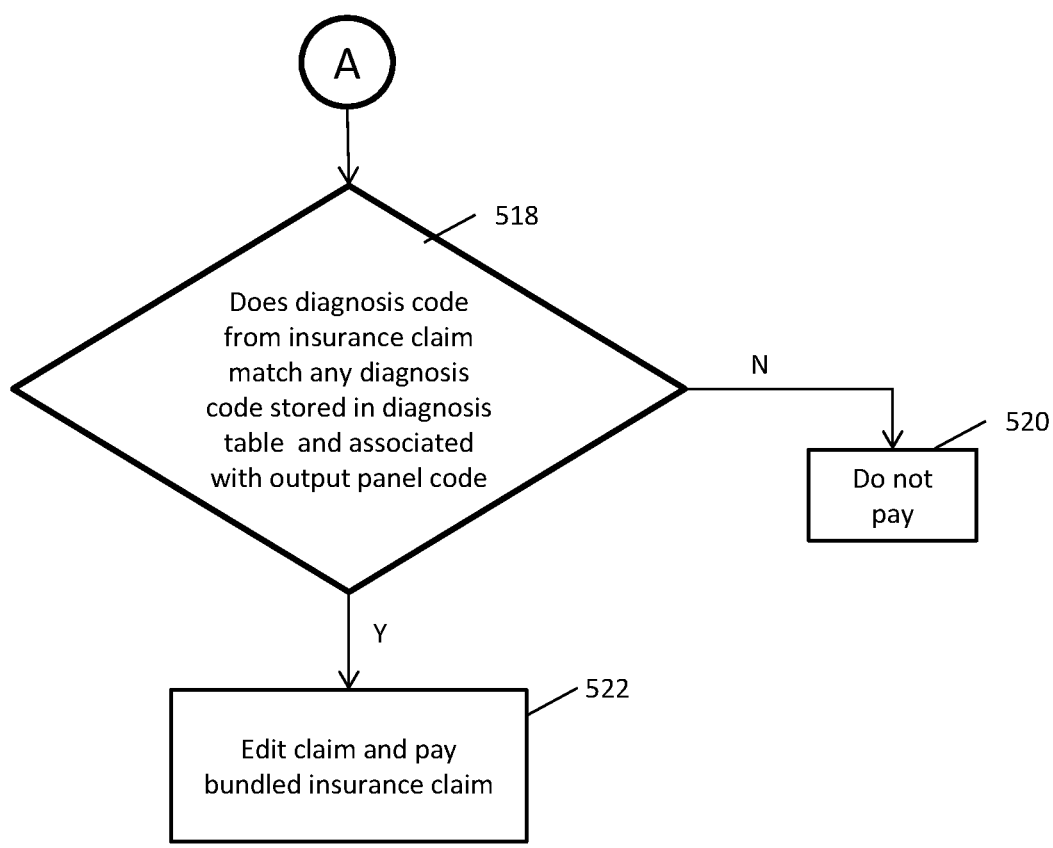

FIG. 5 illustrates a method 500 for editing insurance claim records related to a genetic panel test according to an example embodiment. The method 500 may be performed by the insurance company device 140, by the benefit manager device 102, partially by the benefit manager device 102 and partially by the insurance company device 140, or may be otherwise performed. For the sake of simplicity, the insurance company device 140 will be described as performing the steps of the method 500, but the embodiments described herein are not so limited.

According to an exemplary embodiment, the insurance company device 140 can receive an insurance claim record relating to genetic testing in step 502. The insurance company device 140 can determine that the insurance claim record relates to genetic testing by recognizing a medical service code (e.g. CPT code) associated with genetic testing in the insurance claim record. If the insurance claim record is unrelated to genetic testing or any other editable insurance claim records, the insurance company device 140 can exit the edit.

Subsequently, the insurance company device 140 can retrieve a first of the plurality of edit tables stored in the insurance storage device 142 having a first level in a hierarchy and determine whether any medical service code in the insurance claim record matches a value stored in the first of the plurality of edit tables in step 604. In some embodiments, the first of the plurality of edit tables can be the only edit table having the first level of the hierarchy, and the first level of the hierarchy can be the highest level of the hierarchy. If the insurance company device 140 is unable to match any medical service code in the insurance claim record to the values stored in the first of the plurality of edit tables, the insurance company device 140 can exit the edit in step 506 and can adjudicate and pay the insurance claim record without bundling or editing the insurance claim record in step 508.

Alternatively, if the insurance company device 140 can match one of the medical service codes in the insurance claim record to one of the values stored in the first of the plurality of edit tables, the insurance company device 140 can retrieve a second and a third of the plurality of edit tables having a second tier and a third tier of the hierarchy, respectively. In some embodiments, the insurance company device 140 can retrieve the third of the plurality of tables only after determining that the insurance claim record reflects a genetic panel test. According to an exemplary embodiment, the first of the plurality of tables can include references or pointers to corresponding tables for each entry or row in the first of the plurality of tables. The first of the plurality of tables can have a relatively small number of entries (e.g. 10-30), and the number of entries in the first of the plurality of tables can correspond to a number of genetic panel tests having been assigned medical service codes. For example, a first column of the first of the plurality of edit tables can list the core identifier medical service codes uniquely associated with genetic panel tests, a second column of the first of the plurality of edit tables can list the second tier edit tables associated with each entry in the first column, and the third column of the first of the plurality of edit tables can list the third tier edit tables associated with each entry in the first column. Associations between entries in each column can be made across rows of the table. Thus, by matching a unique identifier, the insurance company device 140 can easily reference the second and third tier tables.

Using these values in the second and third columns, the insurance company device 140, in step 510, can retrieve the second and third tier tables associated with the matched entry determined in step 504. Subsequently, the insurance company device 140 can determine whether a sufficient number (e.g. 1-5) of medical service codes in the insurance claim record match entries stored in the second tier table. If the insurance company device 140 determines that fewer than the sufficient number of medical service codes is stored in the second tier table, the insurance company device 140 can exit the edit in step 506. Alternatively, if the insurance company device 140 determines that the second tier table stores more than or equal to the sufficient number of medical service codes, the insurance company device 140 can determine that the insurance claim record reflects a genetic panel test, and the insurance company device 140 can output the determined genetic panel test in step 514. In some embodiments, the insurance company device 140 outputs the genetic panel test by outputting a medical service code corresponding to the determined genetic panel test. In some embodiments, each row in a fourth column of the first of the plurality of edit tables can include a genetic panel test medical service code.

Furthermore, the insurance company device 140 can compare all medical service codes in the insurance claim record to determine which medical service codes in the insurance claim record match entries stored in any of the first, second, or third tier tables in step 516. Any medical service codes in the insurance claim record that match entries stored in the first, second, or third tier tables can be omitted from the insurance claim record and replaced with the genetic panel test medical service code. Any codes that are not stored in the first, second, or third tier tables can remain in the insurance claim record.

Subsequently, the insurance company device 140 can retrieve a diagnosis code (e.g. ICD10 code) from the insurance claim record and compare the diagnosis code in the insurance claim record to one or more diagnosis claims associated with the genetic panel in step 518. A diagnosis table can store all the diagnosis codes associated with each genetic panel test. If the diagnosis code from the insurance claim record does not match one of the diagnosis codes associated with the genetic panel test, the insurance company can determine that the genetic panel test was medically unnecessary and refer the claim for a clinical review by an appropriately credentialed clinician before making a final determination to pay or not pay the claim in step 520. Alternatively, if the diagnosis code from the insurance claim record matches one of the diagnosis codes associated with the genetic panel test, the insurance company can determine that the genetic panel test was medically necessary and pay the bundled insurance claim, as represented by the insurance claim record, in step 522.

If the insurance claim record includes any medical service codes unrelated to the medically unnecessary genetic panel test, the insurance company device 140 can pay for those other medical service, but not for the genetic panel test prior to additional clinical review. Additionally, the insurance company device 140 can determine whether these other medical service codes are medically necessary or unnecessary before remitting payment. Additionally, the insurance company device 140 can pay for other medical services as well as a medically necessary genetic panel test if an insurance claim record lists a genetic panel test and other medical services.

While the exemplary embodiments are described as having three tiers and a diagnosis table, the exemplary embodiments can include more tiers if additional tiers are required to reduce processing or to differentiate between similar genetic panel tests.

In this manner, because the number of entries in each table increases in each tier, the amount of processing necessary to edit a claim is significantly reduced. Only after determining that an edit is highly likely, the insurance company device 140 continues to process larger amounts of data, but again using only a subset of data and tables stored in a database. Therefore, the data is organized into a hierarchy to significantly reduce the amount of processing necessary to edit an insurance claim record.

FIG. 6 illustrates a method 600 for editing claim records based on a method for genetic modeling (described in greater detail below related to FIG. 7) according to an example embodiment. The method 600 may be performed by the insurance company device 140, by the benefit manager device 102, partially by the benefit manager device 102 and partially by the insurance company device 140, or may be otherwise performed. For the sake of simplicity, the insurance company device 140 will be described as performing the steps of the method 500, but the embodiments described herein are not so limited.

According to an exemplary embodiment, the insurance company device 140 can receive a claim code (see 802*a* . . . *n* in FIG. 8) from a claim record (see 800 in FIG. 8) in step 602. Subsequently, the insurance company device 140 can determine if the claim code received in step 602 is in a genetic model in step 604. If the claim code is unrelated to genetic testing or any other editable insurance claim records, the insurance company device 140 can exit the edit in step 606 and flag the claim code as unmodified (see 806 in FIG. 8) in the claim record (see FIG. 8) in step 608.

Subsequently, the insurance company device 140 can retrieve a first tier record (see FIG. 7) of a plurality of genetic models stored in the insurance storage device 142 and determine whether the claim code matches a value stored in the first tier record in step 610. If the insurance company device 140 is unable to match the claim code to any values stored in the first tier record, the insurance company device 140 can exit the edit in step 606.

Alternatively, if the insurance company device 140 can match the claim code to one of the values stored in the first tier record, the insurance company device 140 can retrieve a second tier record (see FIG. 7) and determine whether the claim code matches a value stored in the second tier record in step 612. In some embodiments, the insurance company device 140 can additionally retrieve the third tier record or an N-tier record after determining that the claim code matches a value stored in the second tier record and determine whether the claim code matches a value stored in the third tier record or N-tier record. FIG. 6 illustrates these steps in dotted lines because they can be optional. Associations between the second tier record and the third tier record can be made, etc.

If the insurance company device 140 determines that the second tier record stores the claim codes, the insurance company device 140 can determine that the insurance claim record reflects a genetic panel test, and the insurance company device 140 can modify a claim record with an output panel code (see 814 in FIG. 8) in step 614. In some embodiments, modifying the claim record can include flagging a modified flag (see 808 in FIG. 8) in the claim record and flagging a genetic panel flag (see 810 in FIG. 8) in the claim record.

Subsequently, the insurance company device 140 can retrieve a diagnosis code (see 802*a* . . . *n* in FIG. 8) (e.g.

ICD10 code) from the claim record and compare the diagnosis code in the claim record to one or more diagnosis claims associated with the panel code in step 616. If the diagnosis code from the claim record does not match one of the diagnosis codes associated with the genetic panel test, the insurance company computer can determine that the genetic panel test was medically unnecessary and flag the claim record for further processing in step 618. Alternatively, if the diagnosis code from the insurance claim record matches one of the diagnosis codes associated with the panel code, the insurance company computer 140 can edit the claim record with the panel code in step 522.

Figure 7:
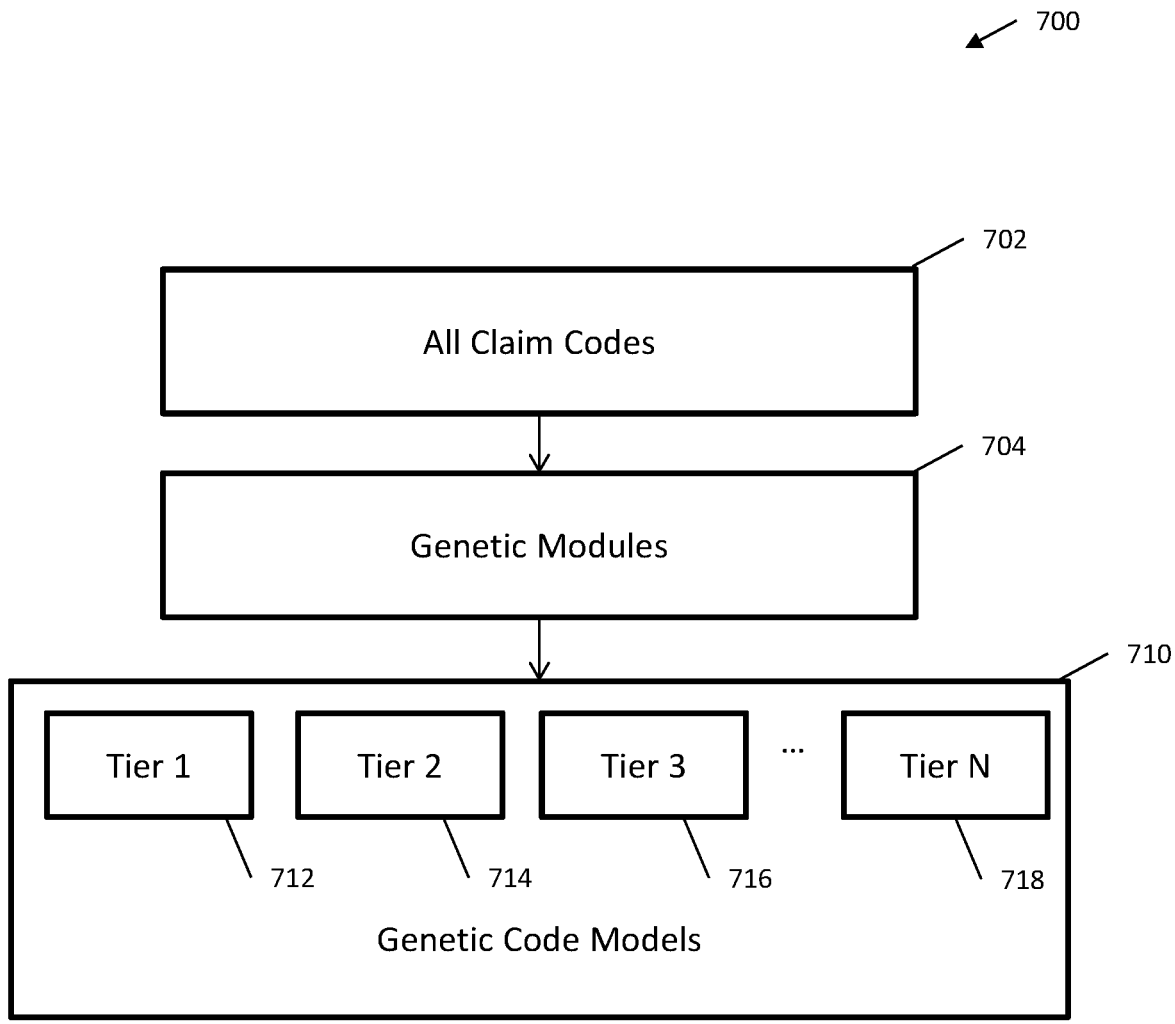
FIG. 7 is a block diagram of a flowchart illustrating methods for creating a genetic claims code model, according to an example embodiment.

FIG. 7 illustrates a flow for creating a genetic claims code model from all claims codes. As shown, all claims codes 702 can be passed to genetic processing modules 704, and the genetic processing modules can process the claims codes to create genetic code models 710. The genetic code modules 704 can group and organize the genetic codes into tiers [1, 2, 3, . . . N] 712, 714, 716, and 718. For example, the first tier 712 can comprise a set of distinct claims codes that can determine if there is a genetic code at all (i.e. whether there is a possibility the claims code indicates a genetic panel test). Tiers 2 and 3 can be organized to help determine whether a genetic panel exists by sorting data into a specific panel test. Different genetic code models 710 can use selected tiers 712-718 with the model, respectively, some tires may overlap and be used in different models. The models 710 are set with the claims computing systems to speed operation on the millions or tens of millions of claims received every day, in an example embodiment, to bundle testing procedures. The models are derived with billions of claims records, which can be over one hundred terabytes of data. The models, in an example embodiment, are needed as the quantity of data to determine accurate models can be too vast for a person to set the models.

Figure 8:
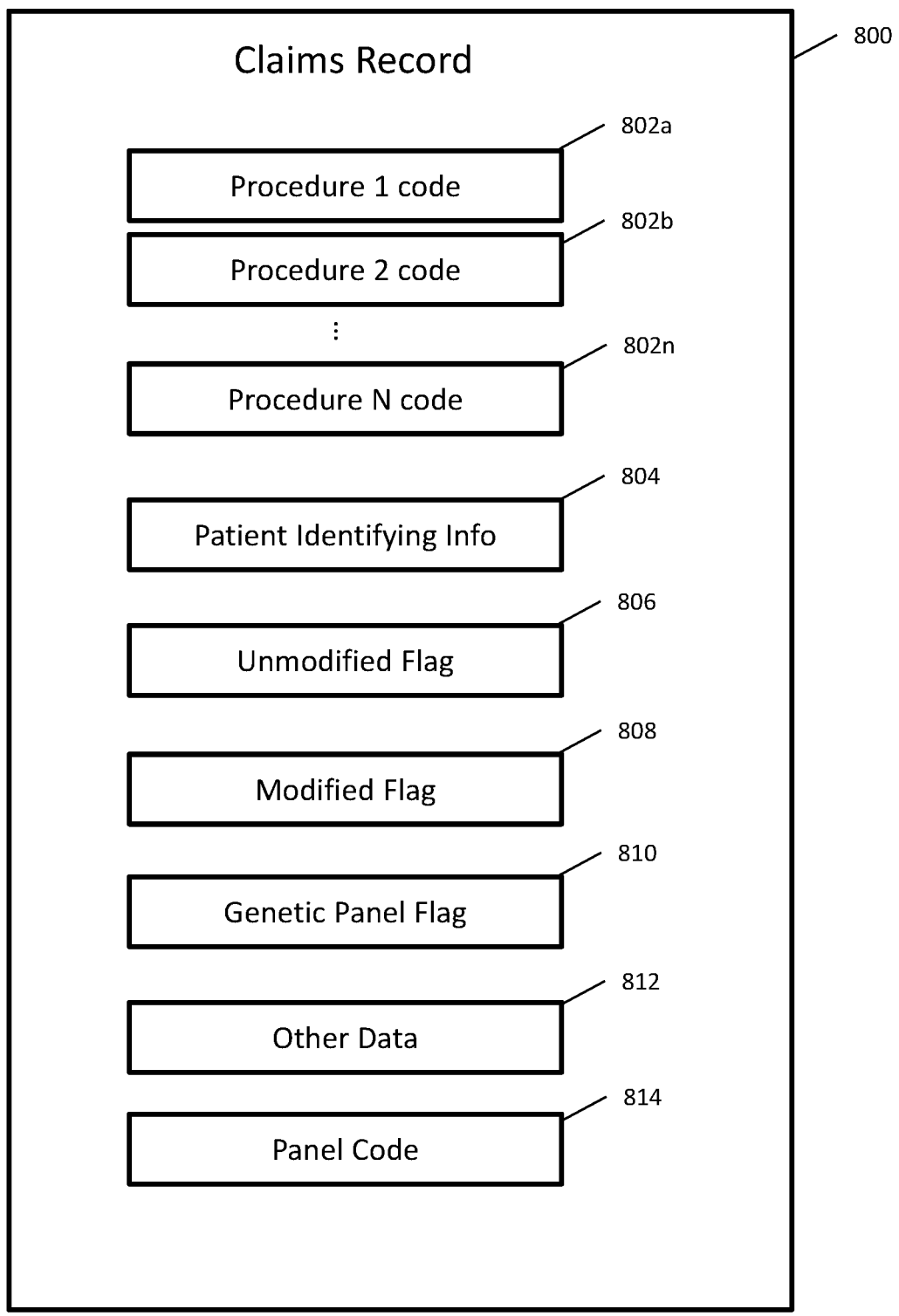
FIG. 8 is a block diagram of a claims record that may be stored within the system of FIG. 1.

FIG. 8 illustrates an exemplary claims record 800. According to an exemplary embodiment, the claims record can include one or more procedure codes 802*a* . . . *n*, patient identifying information 804, an unmodified flag 806, a modified flag 808, a genetic panel flag 810, other data 812, and a panel code 814. The flags 806, 808 can be a same record entry with a first value, e.g., a zero value, indicating that the claims being reviewed using the processes and models described herein are not modified (e.g., not bundled) and with a second value, e.g., a one value, indicating that the multiple claims are bundled together for processing. This flag can control how further processing of these claim records or for a patient are processed in the future. In an example embodiment, the flag 808 is set by at least one of the processes described with reference to FIG. 5*a*, 5*b* or 6. The entire claims record 800 can be modified by the processes and models described herein.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A method comprising:
   receiving, at a processor, an insurance claim record having a plurality of medical service codes;
   retrieving a first of a plurality of electronic edit tables from a computerized database;
   determining, at the processor, whether one of the plurality of medical service codes in the insurance claim record matches one of a plurality of core identifier values stored in the first of the plurality of electronic edit tables;
   in response to determining that the one of the plurality of medical service codes in the insurance claim record matches the one of the plurality of core identifier values stored in the first of the plurality of electronic edit tables, retrieving a second of the plurality of electronic edit tables from the computerized database, the second of the plurality of electronic edit tables indicated by data associated with the one of the plurality of core identifier values determined to match the one of the plurality of medical service codes in the insurance claim record;
   determining, at the processor, whether a number of the plurality of medical service codes match a plurality of confirmation values stored in the second of the plurality of electronic edit tables; and
   editing, at the processor, the insurance claim record by including a genetic panel test medical service code in the record in response to determining that at least the number of the plurality of medical service codes match the plurality of confirmation values stored in the second of the plurality of electronic edit tables.

2. The method of claim 1 further comprising:
   retrieving, at the processor a third of the plurality of electronic edit tables from the computerized database, the third of the plurality of electronic edit tables also being related to the one of the plurality of core identifier values; and
   comparing, at the processor, the plurality of medical service codes to the plurality of core identifier values stored in the first of the plurality of electronic edit tables, the plurality of confirmation values stored in the second of the plurality of electronic edit tables, and a plurality of association codes stored in the third of the plurality of electronic edit tables.

3. The method of claim 2 wherein editing the insurance claim record comprises deleting, at the processor, any of the plurality of medical service codes that match any of the plurality of core identifier values stored in the first of the plurality of electronic edit tables, the plurality of confirmation values stored in the second of the plurality of electronic edit tables, and the plurality of association codes stored in the third of the plurality of electronic edit tables.

4. The method of claim 1 further comprising:
   retrieving, at the processor, a diagnosis table; and
   comparing, at the processor, a diagnosis code included in the insurance claim record to one or more diagnosis code values stored in the diagnosis table and associated with the genetic panel test medical service code.

5. The method of claim 4 further comprising editing, at the processor, the insurance claim record when the diagnosis code included in the insurance claim record matches the one or more diagnosis code values associated with the genetic panel test medical service code.

6. The method of claim 4 wherein the diagnosis code comprises an ICD10 code.

7. The method of claim 1 wherein the plurality of medical service codes comprise CPT codes.

8. The method of claim 1 wherein the plurality of electronic edit tables comprises a hierarchy, a first tier in the hierarchy comprises the first of the plurality of electronic edit tables, and a second tier in the hierarchy comprises the second of the plurality of electronic edit tables.

9. The method of claim 8 wherein the second tier comprises the second of the plurality of electronic edit tables and at least another of the plurality of electronic edit tables.

10. The method of claim 9, wherein the second tier comprises a first number of electronic edit tables that corresponds to a second number of core identifier values in the plurality of core identifier values.

11. A system comprising:
a computerized database configured to store a plurality of electronic edit tables; and
a processor configured to (a) receive an insurance claim record having a plurality of medical service codes, (b) retrieve a first of the plurality of electronic edit tables from the computerized database, (c) determine whether one of the plurality of medical service codes matches one of a plurality of core identifier values stored in the first of the plurality of electronic edit tables, (d) in response to the processor determining that the one of the plurality of medical service codes in the insurance claim record matches the one of the plurality of core identifier values stored in the first of the plurality of electronic edit tables, retrieve a second of the plurality of electronic edit tables from the computerized database, the second of the plurality of electronic edit tables indicated by data associated with the one of the plurality of core identifier values determined to match the one of the plurality of medical service codes in the insurance claim record, (e) determine whether a set of the plurality of medical service codes match a plurality of confirmation values stored in the second of the plurality of electronic edit tables, and (f) edit the insurance claim record by including a genetic panel test medical service code in the insurance claim record in response to the processor determining that at least the number of the plurality of medical service codes match the plurality of confirmation values stored in the second of the plurality of electronic edit tables.

12. The system of claim 11 wherein the processor is further configured to:
retrieve a third of the plurality of electronic edit tables from the computerized database, the third of the plurality of electronic edit tables also being related to the one of the plurality of core identifier values; and
compare all of the plurality of medical service codes to the plurality of core identifier values stored in the first of the plurality of electronic edit tables, the plurality of confirmation values stored in the second of the plurality of electronic edit tables, and a plurality of association codes stored in the third of the plurality of electronic edit tables.

13. The system of claim 12 wherein the processor is further configured to delete any of the plurality of medical service codes that match any of the plurality of core identifier values stored in the first of the plurality of electronic edit tables, the plurality of confirmation values stored in the second of the plurality of electronic edit tables, and the plurality of association codes stored in the third of the plurality of electronic edit tables.

14. The system of claim 11 the processor is further configured to:
retrieve a diagnosis table; and
compare a diagnosis code included in the insurance claim record to one or more diagnosis code values stored in the diagnosis table and associated with the genetic panel test medical service code.

15. The system of claim 14 wherein the processor edits the insurance claim record when the diagnosis code included in the insurance claim record matches the one or more diagnosis code values associated with the genetic panel test medical service code.

16. The system of claim 14 wherein the diagnosis code comprises an ICD10 code.

17. The system of claim 11 wherein the plurality of medical service codes comprise CPT codes.

18. The system of claim 11 wherein the plurality of electronic edit tables comprises a hierarchy, a first tier in the hierarchy comprises the first of the plurality of electronic edit tables, and a second tier in the hierarchy comprises the second of the plurality of electronic edit tables.

19. The system of claim 18 wherein the second tier comprises the second of the plurality of electronic edit tables and at least another of the plurality of electronic edit tables.

20. The system of claim 19, wherein the second tier comprises a first number of electronic edit tables that corresponds to a second number of core identifier values in the plurality of core identifier values.

21. A non-transitory machine-readable medium comprising instructions, which, when executed by one or more processors, cause the one or more processors to perform the following operations:
receive an insurance claim record having a plurality of medical service codes;
retrieve a first of the plurality of electronic edit tables from the computerized database;
determine whether one of the plurality of medical service codes matches one of a plurality of core identifier values stored in the first of the plurality of electronic edit tables;
in response to the one or more processors determining that the one of the plurality of medical service codes in the insurance claim record matches the one of the plurality of core identifier values stored in the first of the plurality of electronic edit tables, retrieve a second of the plurality of electronic edit tables from the computerized database, the second of the plurality of electronic edit tables indicated by data associated with the one of the plurality of core identifier values determined to match the one of the plurality of medical service codes in the insurance claim record;
determine whether a set of the plurality of medical service codes match a plurality of confirmation values stored in the second of the plurality of electronic edit tables, and
edit the insurance claim record by including a genetic panel test medical service code in the insurance claim in response to determining that at least the number of the plurality of medical service codes match the plurality of confirmation values stored in the second of the plurality of electronic edit tables.

* * * * *